United States Patent
Brugger et al.

(10) Patent No.: US 7,025,750 B2
(45) Date of Patent: *Apr. 11, 2006

(54) SET FOR BLOOD PROCESSING

(75) Inventors: James M. Brugger, Newburyport, MA (US); David S. Utterberg, Seattle, WA (US); William J. Schnell, Libertyville, IL (US); G. Keith Andrews, Coupeville, WA (US)

(73) Assignee: DSU Medical Corporation, Las Vegas, NV (US)

( * ) Notice: Subject to any disclaimer, the term of this patent is extended or adjusted under 35 U.S.C. 154(b) by 65 days.

This patent is subject to a terminal disclaimer.

(21) Appl. No.: 10/076,192

(22) Filed: Feb. 13, 2002

(65) Prior Publication Data

US 2002/0072718 A1    Jun. 13, 2002

Related U.S. Application Data

(63) Continuation-in-part of application No. 09/432,555, filed on Nov. 3, 1999.

(51) Int. Cl.
*A61M 5/00*    (2006.01)

(52) U.S. Cl. ..................... 604/246; 604/4.01

(58) Field of Classification Search ............. 604/4.01, 604/6.09, 5.01, 6.1, 905, 251–258, 246, 93.01
See application file for complete search history.

(56) References Cited

U.S. PATENT DOCUMENTS

| | | | |
|---|---|---|---|
| 3,581,733 A | 6/1971 | Grandjean | |
| 3,863,504 A | 2/1975 | Borsanyi | |
| 3,996,027 A | 12/1976 | Schnell et al. | |
| 4,055,176 A | 10/1977 | Lundquist | |
| 4,300,572 A | 11/1981 | Knighton | |
| 4,431,009 A | 2/1984 | Marino, Jr. et al. | |
| 4,432,766 A | 2/1984 | Bellotti et al. | |
| 4,444,198 A | 4/1984 | Petre | |
| 4,519,792 A * | 5/1985 | Dawe .................. | 604/152 |
| 4,710,164 A | 12/1987 | Levin et al. | |
| 5,061,365 A * | 10/1991 | Utterberg ............. | 210/90 |
| 5,067,491 A | 11/1991 | Taylor, II et al. | |
| 5,148,811 A | 9/1992 | Messinger | |
| 5,334,315 A | 8/1994 | Matkovich et al. | |
| 5,370,123 A | 12/1994 | Shinzato | |
| 5,392,653 A | 2/1995 | Zanger et al. | |
| 5,520,640 A * | 5/1996 | Utterberg ............. | 604/80 |
| 5,580,460 A | 12/1996 | Polaschegg | |
| 5,693,008 A | 12/1997 | Brugger et al. | |
| 5,823,967 A | 10/1998 | McArthur | |
| 5,849,065 A * | 12/1998 | Wojke .................. | 96/211 |
| 5,895,368 A | 4/1999 | Utterberg | |
| 5,951,519 A | 9/1999 | Utterberg | |
| 5,951,870 A | 9/1999 | Utterberg | |

(Continued)

FOREIGN PATENT DOCUMENTS

EP    0728509  * 2/1996
WO    WO 01/32256    5/2001

*Primary Examiner*—LoAn H. Thanh
(74) *Attorney, Agent, or Firm*—Garrettson Ellis; Seyfarth Shaw LLP

(57) ABSTRACT

A tubular medical set as main blood flow tubing, a connected, flexible branch tube, a flow restriction device to suppress pressure pulses. The device is positioned to control flow through the branch tube. The flow restriction device permits substantially free, unhindered flow from the branch tube to the main blood flow tubing, while significantly restricting, but not completely blocking, flow from the main blood flow tubing to the branch tube.

19 Claims, 6 Drawing Sheets

U.S. PATENT DOCUMENTS

| | | | |
|---|---|---|---|
| 6,053,967 A * | 4/2000 | Heilmann et al. | 96/208 |
| 6,187,198 B1 | 2/2001 | Utterberg | |
| 6,322,551 B1 | 11/2001 | Brugger | |
| 6,383,158 B1 | 5/2002 | Utterberg et al. | |
| 6,514,225 B1 * | 2/2003 | Utterberg et al. | 604/6.16 |
| 6,517,508 B1 * | 2/2003 | Utterberg et al. | 604/4.01 |

* cited by examiner

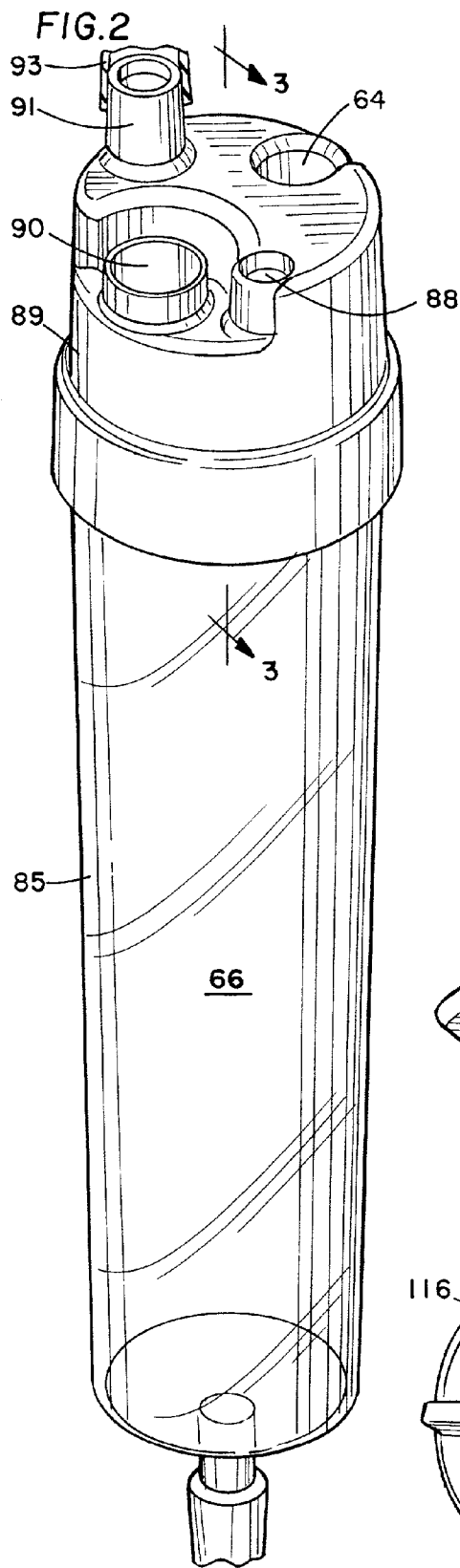
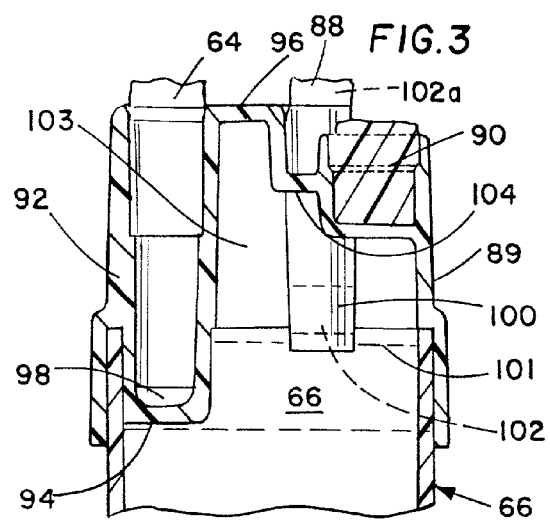
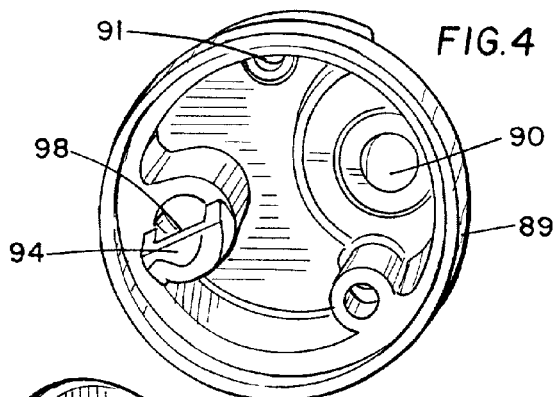
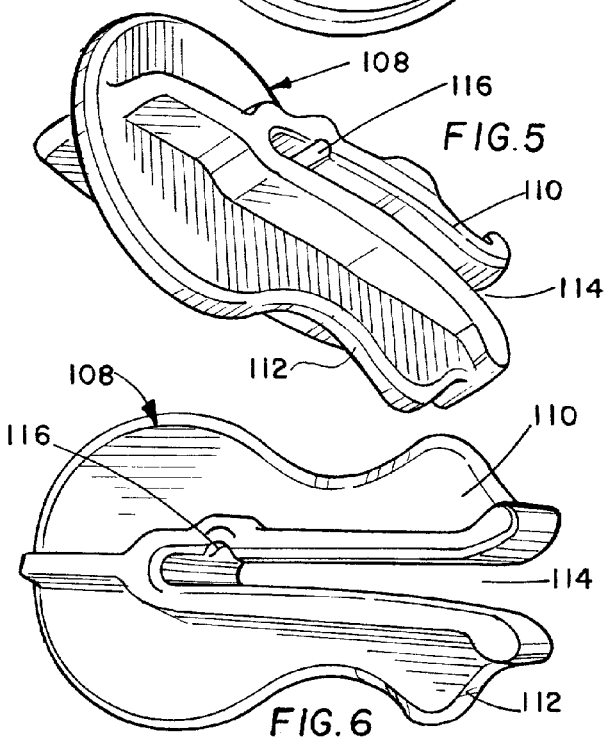

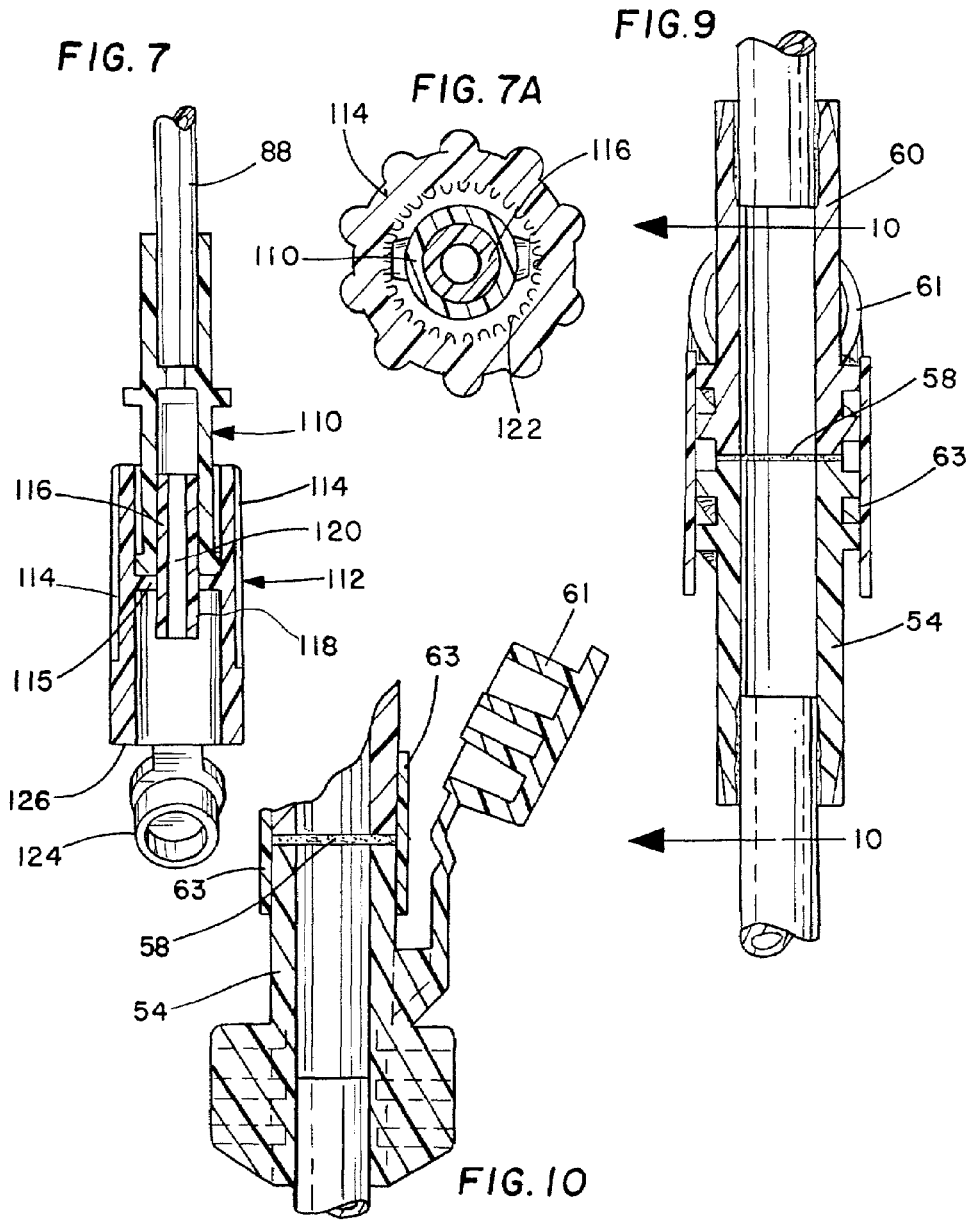
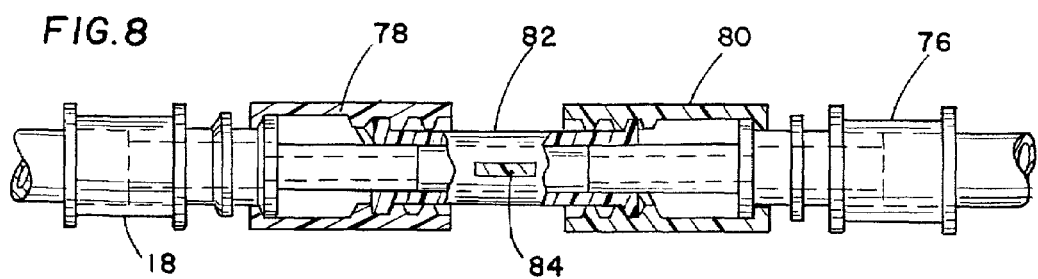

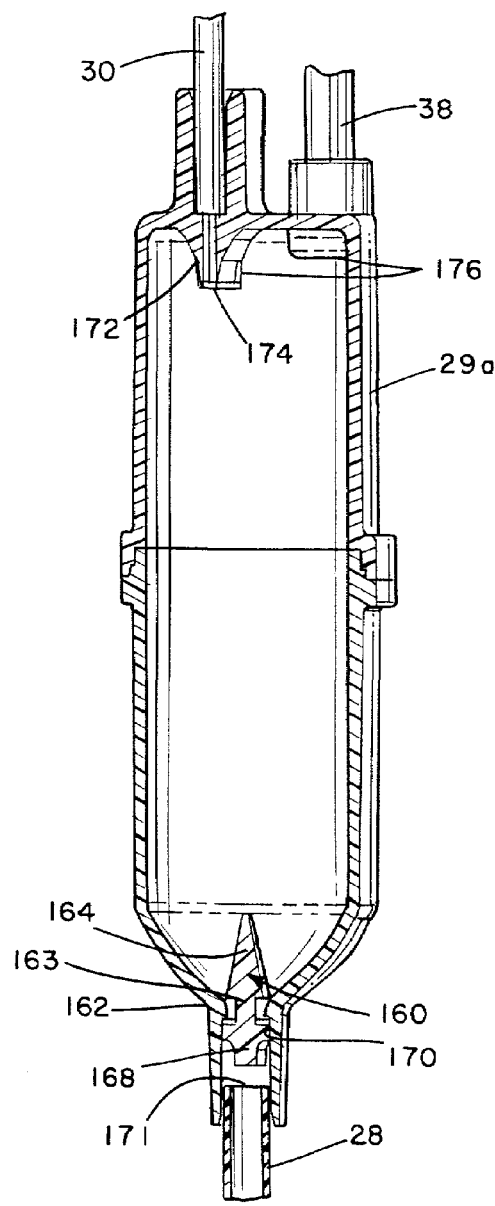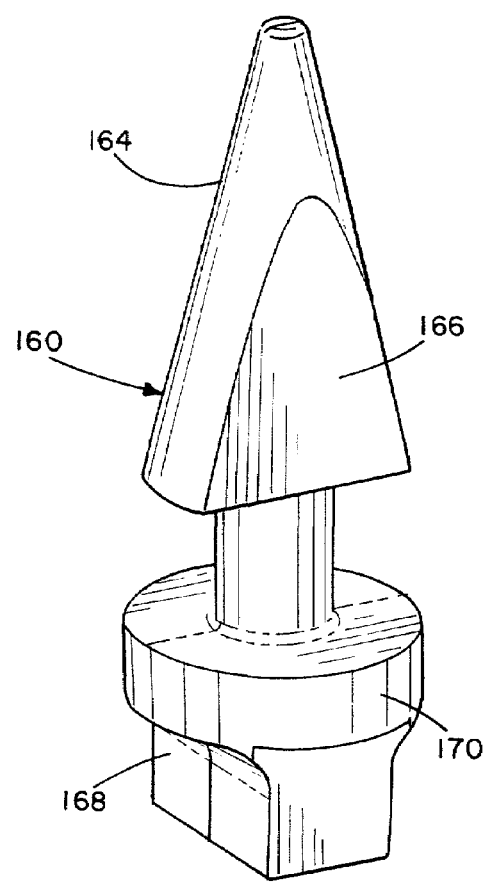
FIG. 17
FIG. 18

SET FOR BLOOD PROCESSING

CROSS REFERENCE TO RELATED APPLICATION

This is a continuation in part of application Ser. No. 09/432,555, filed Nov. 3, 1999, now U.S. Pat. No. 6,517,508.

BACKGROUND OF THE INVENTION

The field of blood processing primarily comprises hemodialysis and plasmapheresis, although other forms of blood treatment may also be used, for example, hemoperfusion, passing blood through adsorbent cartridges, and the like. To accomplish this, blood sets are used to convey blood from the patient to a blood processing device, and then to return the blood from the device back to the patient. The former blood set is called the arterial set, while the latter set is called the venous set.

In combination, the arterial and venous sets comprise several yards of tubing, and thus are rather cumbersome to handle. Furthermore, cost is of course a critical matter, especially when a patient has a chronic need for treatment as in hemodialysis, so that even small cost savings can add up to a substantial amount over a year or more of repeated usage of disposable arterial and venous sets.

Furthermore, priming of the sets is an issue requiring the skilled attention of technicians, so that any improvement or simplification in the priming process, and other processes of use of the arterial and venous sets, can be valuable.

By this invention, numerous improvements to conventional arterial and venous blood sets are provided for reduction of cost and improved ease and efficiency of use.

DESCRIPTION OF THE INVENTION

By this invention, a combined arterial and venous blood tubing set may be provided for the transport of blood between a patient and a blood processing unit. The combined set comprises an arterial set component which comprises arterial tubing having an arterial patient connector at one end and an arterial unit connector at the other end. A venous set component of the set comprises venous tubing having a venous patient connector at one end and a venous unit connector at the other end.

In accordance with this invention, the arterial and venous patient connectors, and the arterial and venous unit connectors, are respectively substantially and releasably directly connected to each other in such manner that the arterial and venous set components cooperate to form a loop.

This facilitates the installation of the sets into a hemodialysis machine, for example, resulting in greater ease of installation with a saving of time. Eventually, the set components wind up serving in the normal manner of arterial and venous sets. Even with a relatively small increase or improvement in ease and time saving, the improvement can be quite substantial particularly in the treatment of chronic conditions, as in most hemodialysis, so that the effect of the improvement in time savings can add up to a substantial amount over the course of a year.

Particularly, the arterial and venous unit connectors may be directly connected together with a frangible seal, to permit their breaking apart after the combined set has been primed, for subsequent connection to a blood processing unit.

Thus, the fully primed arterial and venous sets may be directly connected to a reused dialyzer. Solution may then be circulated through the system with air being removed from the dialyzer, but no air being sent to the dialyzer through the primed sets, which reduces the number of air bubbles being trapped within the dialyzer itself. Air coming from the dialyzer will then be typically removed by a bubble trap in the sets, so that it is not recirculated again to the dialyzer.

By this invention, particularly wet, reused dialyzers (or other blood processing devices) can be effectively primed to exhibit improved performance because of a reduced number of trapped air bubbles within the membrane system of the dialyzer.

The arterial and venous patient connectors of the respective arterial and venous sets may optionally be substantially directly connected together by an interconnector tube to permit circulatory priming of the arterial and venous sets, and also to avoid the need of other end closures at the arterial and venous patient connectors, if the arterial and venous sets are supplied to the user in interconnected form as in this invention.

The interconnector tube preferably comprises a tube having a connector such as a female luer connector at each end, for connection with the patient connectors of the arterial and venous sets. Also, the tube may have an attached, integral cap to close an end of the tube after disconnection of one of the patient connectors. Thus, one of the patient connectors may have its sterility preserved while the other patient connector is being attached to a fistula set and access to the patient's bloodstream is being obtained.

Priming of the connected arterial and venous sets can be performed in a manner similar to that disclosed in Utterberg U.S. Pat. No. 5,951,870, preferably with the modifications described below:

The arterial and venous sets respectively preferably have the substantially directly connected end connectors to form a closed loop as described above. One may pass priming solution into and through a portion of the directly connected arterial and venous sets in a first direction that is reversed to the normal direction of blood flow through the sets, while removing air from one of the sets through a branching port from one of the sets.

One also may pass priming solution into a second direction of flow opposite to the first flow direction through the system (which opposite direction is the normal direction of flow through the system) while continuing to remove air from the system through the port, until substantially all air desired is removed from the arterial and venous sets.

Thereafter, with the flow stopped temporarily the unit arterial and venous connectors are separated and connected to the blood processing unit such as a dialyzer preferably with the blood outlet at the top to facilitate bubble removal. One then pumps the priming solution through the arterial and venous sets and the blood processing unit in the second flow direction (i.e., the normal flow direction which is reversed to the first flow direction), to flush the sets and blood processing unit, without passing substantial amounts of air into the blood processing unit.

This method can be accomplished while pumping the solution with a flow pump such as a roller pump through the set, which operates in only a single, pumped flow direction throughout the entire priming process, the normal, second flow direction described above. The first flow direction, which is reverse to the second flow direction, may take place by gravity flow if desired. Preferably, the arterial and venous patient connectors are substantially directly connected together throughout substantially all of the performance of the above method.

The invention also pertains to a tubular medical fluid set having an in-line bubble trap chamber having a top wall. The top wall defines a port which communicates with flow tubing of the tubular set. The port communicates with a port tube which extends into the chamber and has a tube end which is spaced below the top wall, and preferably below the intended blood/air interface. The tube end defines a wall that directs flow out of the tube circumferentially into and through the bubble trap chamber. Thus, blood entering the chamber through the tube is directed circumferentially about the chamber wall, the effect of which is to direct bubbles radially inwardly, rather than downward.

The chamber also preferably defines a baffle to convert circumferential flow into turbulent flow at positions above the tube end wall and the circumferentially directed blood and at the blood-air interface. This prevents formation of a blood whirlpool having a significant, centrally depressed upper surface. Thus, the centrally disposed bubbles will rise to the top of the chamber to join an air space that is typically present there, without being sucked downwardly as would be caused by the presence of such a blood whirlpool having a centrally depressed upper surface.

Accordingly, the flow pattern of blood near the top of the bubble trap chamber described comprises a top segment of largely turbulent blood flow, and a lower segment of largely circumferential blood flow.

As another aspect of this invention, priming of a tubular medical fluid set may take place, the set having an in-line bubble trap chamber, preferably on the venous set. One passes priming solution into the tubular set preferably at a point pre-pump on the arterial set and bubble trap chamber, while withdrawing air from the set through a port in an upper portion of the chamber. The port communicates with a port tube extending into the chamber in positions which are spaced below a top chamber wall.

Further in accordance with this invention, preferably the in-line bubble trap chamber has an upper portion which defines a port that communicates with the exterior. The port communicates with a port tube extending into the chamber, having a port tube opening spaced below the top wall within the chamber, to automatically define a predetermined air volume and liquid level in the chamber approximately at or above the tube opening as the tubular set is filled with priming solution.

The bubble trap chamber top wall also may define an axially depressed portion which, in turn, defines a needle pierceable, resealable injection site to permit an injection needle of at least about ½ inch needle length to penetrate said injection site and to communicate with liquid below said liquid level which preferably is set by the port tube arrangement mentioned above.

Contrary to the prior art, this injection site carried on the top wall of a bubble trap chamber resides at a lower position from other portions of the top wall, providing a desired inner volume under the other portions for air above a liquid level. In combination with this, the resealable injection site is carried on the axially depressed portion of the top wall, so that the injection site is closer to the liquid level within the bubble trap chamber, preferably permitting an injection needle of at least about ½ inch needle length to penetrate the injection site and to communicate with the liquid below the liquid level, while still permitting an air volume within the bubble trap chamber of preferably at least about 4 cc. This permits direct access to the blood by a conventional hypodermic needle from the top of the chamber, for blood sampling from the chamber injection site, permitting infusion of the very expensive drug erythropoietin ("EPO"), with pump flushing of the needle several times, drawing blood into the needle and out again to rinse all possible EPO into the set and then the patient, to avoid wasting of the highly valuable material.

Further in accordance with this invention, a tubular blood set for transfer of blood between a patient and a blood treatment device has main blood flow tubing and a flexible branch tube connected in branching relation to the main tubing. The branch tube is adapted for connection at its other end to a source of physiological, cell-free solution, as is conventional.

As particularly shown in Utterberg et al pending patent application Ser. No. 09/203,274, filed Dec. 1, 1998, some of the blood passing through the main blood flow tubing may extend into the branch tube to form a blood-solution interface, so that a pressure monitor which is also connected to the branch tube is protected from contact with blood by the presence of an amount of cell-free solution in the branch tube and a non-compressible, air-free pressure sensing path is provided through the cell free solution and the blood across the interface.

In accordance with this invention, to suppress pressure pulses from the main blood line tending to disrupt the blood-solution interface, a portion of the flexible branch tube is equipped with pulse suppression means. Such means may comprise a partially collapsible portion of the branch tube, a ball valve, a duckbilled valve or the like. The required aspects of the flattened tube or valve are that relatively unrestricted flow is allowed from an attached saline bag to the bloodline but flow from the blood line to the branch tube is suppressed progressively as the negative pressure in the blood line increases. To preferably accomplish this, the pulse—suppressing portion of the flexible branch tube is substantially flattened. Accordingly, this tube portion has a lumen that can and does reduce its cross-sectional area responsive to negative pressure in that area to a degree substantially greater than cylindrical tubing. This results in the suppression of negative pressure pulses created by the pumping of blood through the main flow tubing, which negative pressure pulses tend to disrupt the blood-solution interface in the branch tube. However, if the tube portion that is flattened is preferably placed in the branch tube between the blood-solution interface and the main blood flow tubing, the effect of these negative pressure pulses is damped at the interface area. However, the tube portion, or an alternative valve, can increase its cross-sectional area at any time responsive to positive pressure. Thus, if there is an urgent need to provide saline solution to the extracorporeal blood flow path in the event of a crisis, the tube portion or valve can expand back to its normal cylindrical shape or seating of the valve is less, so that increased solution flow can pass therethrough.

The flattened branch tube portion may comprise a flattened lumen cross section that defines a periphery having at least one open groove, which is transverse to the cross section, to avoid complete closing of the branch tube under negative pressure. Furthermore, a generally cylindrical, flexible branch tube may be used, the tube being flattened at the tube portion by a removable slide clamp which comprises a pair of arms defining a slot between them. The tube portion resides in the slot and, as is preferable, at least one of the arms defines a transversely extending groove that forms the open groove in the tube portion.

Basically, there is no limit to the types of structures that can be used in a valve function to provide relatively unrestricted flow from an attached saline bag to the blood line as needed, but also suppressing reverse flow from the blood line to the branch tube that connects to the saline bag, to suppress fluid pressure pulses particularly at the blood-solution interface, as previously discussed. Particularly, such a valve member closes to restrict flow (but not completely close) when pressure conditions for reverse flow are present, but it opens wide under forward flow pressure so that solution may be quickly added to the blood line. Thus, hypotensive patients may receive saline quickly through the system if that is needed, but the same system restricts blood from the blood line from pushing up the branch line by pressure oscillations, which mix the blood and the solution and destroy the discreet blood-solution interface. However, such a valve member allows enough reverse flow so that line pressures are equilibrated above the blood-solution interface quickly, so that a hazardous pressure situation is recognized by the pressure transducer.

Typically, such a valve allows full, rapid, 100 percent flow downstream through the branch tube from the solution source to the blood line, but only allows between about one to fifty percent of that flow in the reverse direction, typically on the order of five to twenty percent of the downward flow toward the blood line, under normal pressure conditions.

Further in accordance with this invention, a protector for a female luer connector is provided, which comprises: an outer sleeve, a central transverse wall defined in the outer sleeve, a male luer projecting axially within the sleeve from the transverse wall to engage the female luer connector along with the sleeve. A tube projects axially within the sleeve from the transverse wall into the direction opposed to the male luer. The tube and the male luer have connected lumens, with the tube having an outer end that is substantially recessed within the sleeve.

Accordingly, a female luer connector may be used as a air venting and/or drain line during priming, for example, with accordance with the teaching of Utterberg U.S. Pat. No. 5,951,870. However, after priming, rather than closing off this line it can be used for the addition of supplemental medication, added solution, or the like because the female luer connector on the end can have its sterility retained by the protector of this invention.

Specifically, the protector of this invention has an outer sleeve inner wall which has screw threads or preferably is free of screw threads. The sleeve inner wall preferably defines axially extending ribs at least on the side of the transverse wall that carries the male luer, to facilitate axially sliding connection and retention with the female luer connector. Furthermore, it is preferred for the tube outer end, which does not need to carry a taper like a male luer, to terminate at a point no more than about two thirds of the distance from the transverse wall to the end of the outer sleeve which is opposed to the male luer, so that this tube serves as a spout for the venting of air and priming solution, and is retained in aseptic condition, since it is recessed in the outer sleeve and thus protected.

Also, it is preferred for a hinged cap to be attached to the outer sleeve in a position which permits closure of the cap over the outer sleeve end that is opposed to the male luer, for preservation of aseptic conditions between priming and subsequent use of the female luer connector.

Thus, sets for blood processing are provided which exhibit significant distinction and advantage over the prior art.

DESCRIPTION OF THE DRAWINGS

Referring to the drawings,

FIG. 2 is a fragmentary, perspective view of the bubble trap chamber of the venous set of FIG. 1;

FIG. 3 is a sectional view taken along line 3—3 of the FIG. 2;

FIG. 4 is a perspective view of the underside of the top cap of the chamber of FIG. 2;

FIGS. 5 and 6 are perspective views of a sliding clip utilized in the set arrangement of FIG. 1.

FIG. 7 is an enlarged longitudinal sectional view taken along line 7—7 of FIG. 1;

FIG. 7A is an enlarged sectional view taken along line 7A—7A of FIG. 1;

FIG. 8 is an enlarged longitudinal sectional view taken along line 8—8 of FIG. 1;

FIG. 9 is an enlarged longitudinal sectional view taken along line 9—9 of FIG. 1; and FIG. 10 is a partial longitudinal sectional view similar to FIG. 9 but rotated 90 degrees about the longitudinal axis.

FIG. 17 is a longitudinal sectional view of an in-line chamber, which may be used in a branch line in accordance with this invention, having a different design for a pulse suppression member.

FIG. 18 is a perspective view of the pulse suppression member used in the chamber of FIG. 17.

DESCRIPTION OF SPECIFIC EMBODIMENTS

Figure 1:
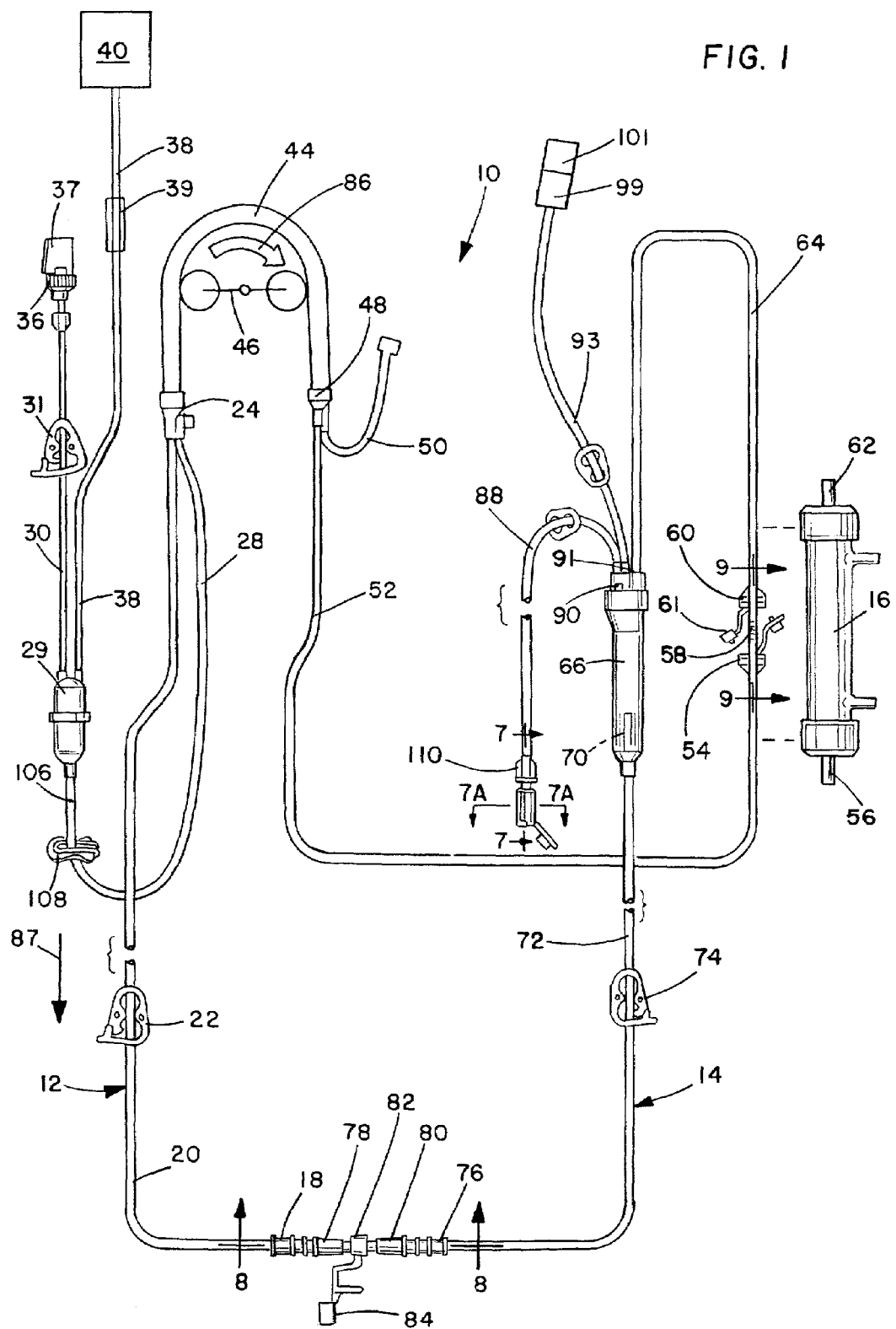
FIG. 1 is a plan view of a combined arterial and venous set system in accordance with this invention, with the respective ends of the arterial and venous sets being connected together to form a closed loop prior to use.
Figure 11:
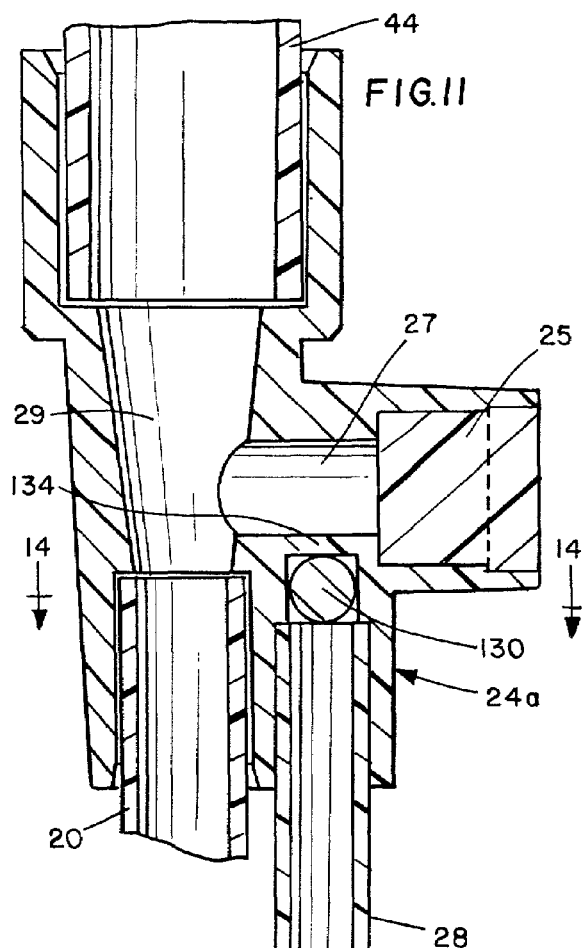
FIG. 11 is a highly enlarged, longitudinal sectional view of a portion of the set system of FIG. 1, showing an alternative embodiment.

Referring to the drawings, FIG. 1 shows a combined arterial set and a venous set 10 for hemodialysis comprising arterial set 12 and venous set 14, which sets may be used in the conventional manner in conjunction with a conventional dialyzer 16 for the performance of hemodialysis. Hemodialyzer 16 may be replaced with a hemoperfusion device or another flow through blood treatment device as may be desired.

Arterial set 12 comprises a patient connector 18, which is connected to set tubing 20, closeable by a conventional pressure clamp 22. Set tubing 20 communicates with connector 24 for roller pump tubing 44 and having a branch tubing 28 extending out from connector 24.

Branch tubing 28 connects with chamber 29, which connects with tubing 30 that communicates with a pressure monitor 37 by connector 36. Chamber 29 also connects with a second branching tube 38, which connects with a source of physiological priming solution 40 for priming of the set, and also for administration to the patient as needed during the dialysis procedure.

Roller pump tubing 44 may be fitted within a roller pump system 46 for pumping of fluid through the set system. Branch tubing 50 may extend from second pump tubing connector 48 for additional connection access to the system, such as for connection to a heparin source. Connectors 24, 48 may be as disclosed in Utterberg U.S. Pat. No. 5,360,395.

Arterial set 12 has an additional length of tubing 52 that extends from roller pump tubing connector 48 to arterial unit connector 54, which is proportioned to connect to arterial end 56 of dialyzer 16. However, by this invention, arterial unit connector 54 is integrally connected with a frangible seal 58 to venous unit connector 60, which is adapted to connect with the venous blood port 62 of dialyzer 16. Preferably, sleeve 63 (FIG. 10) surrounds the frangible section to help prevent touch contamination of the sterile areas during franging (breaking apart). Thus, in an initial condition as shown, unit connectors 54, 60 are initially connected together, being frangibly breakable along line 58, which then subsequently permits them to be connected to the respective ports 56, 62 of dialyzer 16 at a desired step in the process of setup of a dialysis system. Each connector 54, 60 has an integral closure cap 61.

Unit connector 60 of venous set 14 connects with flexible tubing 64, and communicates into venous bubble removal chamber 66 through the top cap thereof. In normal flow, blood in chamber 66 passes through filter 70 and into venous tubing 72, closeable by conventional squeeze clamp 74, to connect to patient venous connector 76. Both patient connectors 18, 76 are essentially directly connected together preferably prior to sterilization of the set by the engagement of their respective threaded sealing caps 78, 80 by means of a tubular double connector tube 82, which provides sealing fluid connection between the respective tubular sets and connectors 18, 76 while permitting disconnection when desired. For example, patient arterial connector 18 may be disconnected from double connector 82, and then cap 84 may pivot around to close double connector 82 to retain sterility in the venous patient connector 76, while arterial patient connector 18 is being joined to a fistula needle, for example, and connection to the patient's fistula is being effected.

In accordance with this invention, the arterial and venous sets 12, 14 are connected together in basically a loop form by the integral joining of unit connectors 54, 60 along frangible line 58, and by the mutual joining of arterial and venous patient connectors 18, 76 with double connector tube 82. Preferably, the set may be received in this form in sterile condition from the manufacturer to the site where the dialysis is to be performed. The system is mounted in a dialysis machine, without connection to dialyzer 16, in the closed loop condition of FIG. 1. Alternatively, connection may be initially made at this point between unit connectors 54, 60 and dialyzer 16, particularly when an internally dry, typically unused dialyzer 16 is provided.

Otherwise, the direct connection between unit connectors 54, 60 may be maintained during the first steps of priming particularly in that situation where dialyzer 16 has a wet interior because it has been previously used, and has been resterilized by conventional processes. Priming solution from container 40 passes through branch tubes 38, 28, filling chamber 29 as well as the rest of the arterial and venous set system by pumping of roller pump 46 to cause solution flow in direction 86. If desired, simultaneously or sequentially in either order, solution may also flow in a reverse direction through tube 20 per arrow 87, typically by gravity solution flow, through the connection between patient connectors 18, 76 and through tubing 72 in direction 87, to fill chamber 66 from the bottom, thus avoiding the trapping of air bubbles in filter 76, with air being vented through branch tubing 88.

By this means, the respective, joined sets 12, 14 can be substantially filled with priming solution, and all undesired air is driven out of the set. Then, if not before, unit connectors 54, 60 may be separated and connected to the respective ports 56, 62 of dialyzer 16, and further circulatory flow may pass through the entire system in direction 86, driven by roller pump 46, for the final recirculation, flushing, and/or rinsing procedure prior to introduction of blood to the system through arterial patient connector 18 and return of blood through connector 76.

A major advantage for performing initial filling and priming of dialysis sets 12, 14 in the form of an interconnected loop without dialyzer 16 results from the fact that priming can then take place without the insertion of additional air through the dialyzer. A wet dialyzer will trap air bubbles in its membrane, resulting in a reduction in dialysis efficiency, so the efficiency is improved by filling the arterial and venous sets 12, 14 first, and then connecting with particularly a wet dialyzer 16 for the completion of the priming process, which process may be conventionally performed from then on. Specifically, flow pump 46 may be a conventional unidirectional pump which pumps in only one flow direction as needed throughout the entire priming process. Bidirectional flow from chamber 29 may take place simultaneously in both directions 86 and 87 if the flow rate of priming solution through tube 28 is greater than the flow rate through pump tubing 44, the excess of the solution flowing in direction 87 through tube 20 for a rapid, bidirectional priming of the respective sets 12, 14.

Referring further to FIGS. 2 through 4, venous bubble removal chamber 66 comprises a body 85, typically with a tubular cross section, and top cap 89, having a series of apertures for connection with tubing. One of such connections comprises main venous flow tubing 64, while another of the connections comprises branch tubing 88, through which venting of air and priming solution may take place during the priming process.

Cap 89 may also define an aperture which holds needle pierceable injection site 90, of conventional design except as otherwise described herein. Port 91 connects to pressure monitor line 93 (FIG. 1).

In accordance with this invention, flow tubing 64 communicates through cap 89 into communication with port tube 92 extending into the interior of chamber 66 and cap 89, having an inner tube end 94 extending below top wall 96 of cap 89. Tube end 94 comprises a wall (of the same reference number) that directs flow through the tube circumferentially of the bubble trap chamber, through side aperture 98. Thus, blood inflowing through tube 92 is directed to flow around the inner circumference of chamber 66.

Branch tube 88 communicates with baffle tube 100, which enters the chamber 66 through top wall 96, and terminates at a level which is preferably closer to top wall 96 than is aperture 98 of inlet tube 92. Thus, baffle tube 100 communicates with the chamber interior, and also serves as a baffle along with tube 92 to convert circumferential flow at its level in chamber 66 into turbulent flow, at positions above tube end wall 94 and aperture 98. Thus, inflowing blood provides a rapidly rotating area of blood at approximately the level of aperture 98. However, at areas nearer to top wall 96, baffle tube 100 and tube 92 interfere with the circumferential flow of blood and cause turbulence, which prevents formation of a blood whirlpool having a significant, centrally depressed upper surface. Nevertheless, the rapid, circumferential flow of blood at the level of aperture 98 and slightly below in chamber 66 causes microbubbles in the blood to be driven to the center of rotation, where the microbubbles can rise upwardly through the turbulent blood area at the level of baffle tube 100, to collect under wall 96 and join in a gas bubble or air space 103 there.

This airspace 103 is spontaneously formed during the priming of this set in chamber 66, which airspace defines a liquid level 101 at about the lower edge of baffle tube 100 at ambient pressure. This is because air is vented out of baffle tube 100 and branch tube 88 during priming. Thus, when sufficient air has been vented so that the blood level rises to reach tube 100, air venting stops. Fluid preferentially passes up tube 100, and the air above the lower end of tube 100 is trapped. Then, during operation under a positive pressure as provided by roller pump 46, the airspace 103 will compress, and the liquid level will rise to a degree above the lower end of tube 100. Thus, the desired liquid level can be spontaneously formed in chamber 66 on priming.

The air in monitor tube 93, transducer filter 99 and the pressure monitoring tubing within the dialysis machine 101 have a fixed air volume.

The position of the tower end of baffle tube 100 and the related position of opening 98 assures that enough air volume at ambient pressure exists in chamber 66 to prevent liquid entering monitor tube 93 when the system is fully pressurized at operating flows. Because cross contamination deaths have occurred when blood from one patient broke through a transducer filter and contacted viruses from a previous patent using the same machine, this invention has great power to save lives. Given the air volume of various machines on the market, the air volume at ambient above tube end 100 within chamber 66 is preferably at least 4cc to attain this safety advantage.

As shown in FIG. 3, top wall 96 of bubble trap chamber 66 defines an axially depressed portion 104 which, in turn, defines the needle pierceable, resealable injection site 90. Thus, a conventional injection needle of at least about ½ inch needle length can be placed through injection site 90 to penetrate the injection site and to communicate with liquid level 101 within chamber 66. As previously described, this permits continuous contact with the blood supply in chamber 66, so that EPO, for example, may be administered within pump-flushing, where blood is drawn into the needle and reintroduced back in to the chamber to rinse virtually all EPO from the interior of the needle and syringe, thus assuring essentially a 100 percent administration of the valuable drug. Air volume in chamber 66 typically of at least 4cc, in combination with the invention of depressed portion 104 for the position of injection site 90, can provide the combined benefits of sufficient chamber volume for antitransducer protector wet-out, and use of ½ inch needles are described above.

Further in accordance with this invention, in FIG. 1 second branch tubing 30 communicates with a conventional pressure monitor 37. As described in the previously cited patent application Ser. No. 09/203,274, it is desirable to connect pressure monitor 37 with a substantially incompressible liquid pressure transfer path through second branch line 30, chamber 29, and branch line 28 without a significant amount of compressible gas such as air being present, except for a small amount of air in the tubing next to the transducer protector so that the transducer protector is not wetted with solution. Also, a small amount of air is present in the tubing of the transducer device itself. As described above, it is highly undesirable for blood to enter pressure monitor 37, which is also connected to dialysis machine 101. Even if a normal protector is used, it is clearly better for the blood to be spaced from pressure monitor 37. To this end, upon priming, second branch line 30 may be filled with priming solution which remains to provide the substantially more incompressible liquid pressure transfer path, and also to space the blood from pressure monitor 37. Thus, upon operation of the arterial and venous sets 12 and 14 to transfer blood, a blood-solution interface 106 may be formed typically in branch line 28, so that a continuous liquid pathway is provided to pressure monitor 37, without the blood getting near to the monitor.

However, the pumping action of roller pump 46 against pump tubing 44 causes an oscillation in the pressures in the sets, including branch lines 28, 30. Because of the higher density of blood relative to that of saline, this oscillation tends to cause the blood-solution interface 106 to break up, with blood mixing into the solution. To address this, a slide clamp 108, shown in FIGS. 1, 5 and 6, may be provided to substantially flatten a portion of branch tube 28, i.e., that portion which occupies the interior of slide clamp 108. Slide clamp 108 is preferably positioned between blood-solution interface 106 and connector 24.

As shown in FIGS. 5 and 6, slide clamp 108 comprises a pair of arms 110, 112 defining a slot 114 between them. The flattened tube portion resides in slot 114. Contrary to other slide clamps, slide clamp 108 is proportioned in slot 114 so that flow is not completely blocked through tube 28, but tube 28 is merely flattened within clamp 108.

It is further preferred for at least one of arms 110, 112, specifically shown to be arm 110, to define a transversely extending groove 116. Groove 116 forms in the flattened portion of branch tube 28 a corresponding open groove which is generally parallel to the longitudinal axis of the branch tubing, to avoid complete closing of the branch tube under negative pressure. Since slide clamp 108 has a slot 114 of a width which does not completely close branch tubing 28, it merely puts the enclosed section of branch tube 28 into a substantially flattened configuration, with the result that negative pressure pulses tend to cause the flattened tubing to transiently and spontaneously lose lumen area by at least partial collapsing, thus damping the effect of the oscillatory pressure and preserving the integrity of precise blood-solution interface 106, while still permitting transfer of pressure in set 12 to sensor 37.

However, in the event of an emergency, where the patient needs solution with utmost urgency on a life-threatening basis, slide clamp 108 can be quickly removed from branch tube 28, and roller clamp 39 can be opened wide for rapid solution administration. The flattened portion of branch tube 28 can expand out to cylindrical shape again, and thus, it does not provide a barrier to high volume solution administration. Additionally, second branch tubing 30 can be put into action to provide added solution, by disconnecting it from pressure monitor 38 and connecting it to a new source of solution.

As another preferred alternative to the use of slide clamp 108 to stabilize blood-solution interface 106 in the presence of oscillatory pressure in the set 10, pump tubing connector 24 can be modified as connector 24a in the manner illustrated in FIGS. 11–14, with slide clamp 108 being not used. Alternatively, another connector or tube of branch line 28 below saline/air interface 106 may be modified in equivalent manner as described below.

Connector 24a connects to pump tubing 44 at one end and to blood flow line 20 at the other end as in the previous embodiment, and injection site 25 is provided, being filled with an elastomeric, needle piercing material. Transverse bore 27 communicates between the centralbore 29 of connector 24a, all in a manner similar to the known design of connector 24.

Also, connector 24a provides a parallel connection to branch line 28 as in the previous embodiment.

Figure 12:
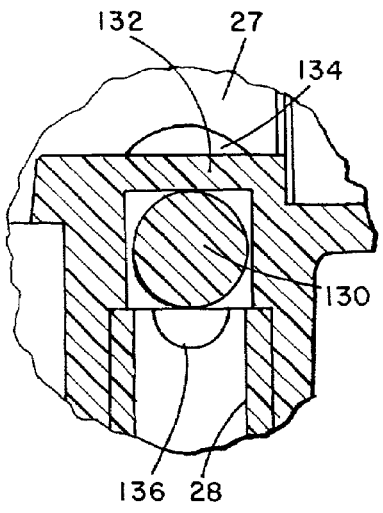
FIGS. 12 and 13 are enlarged portions of FIG. 11, showing the range of motion of a valve ball.
Figure 13:
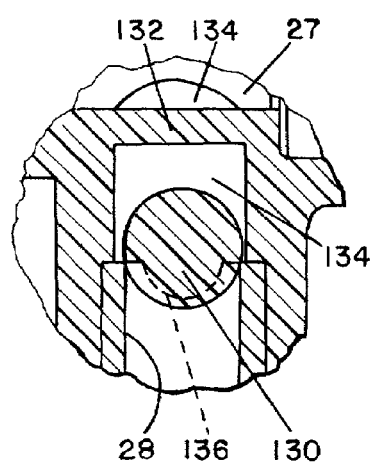
Figure 14:
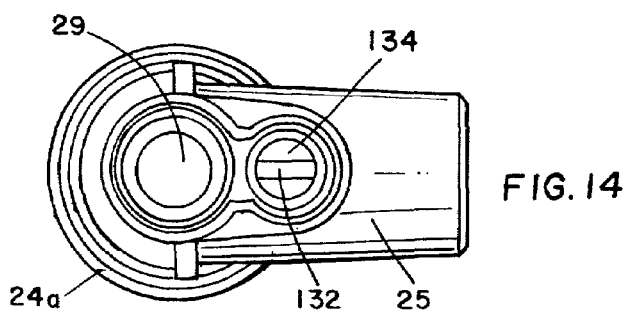
FIG. 14 is a sectional view taken along line 14—14 of FIG. 11, with the valve ball omitted.

By way of modification, connector 24a carries a valve which comprises a ball 130, which is trapped in a space 134 that communicates with branch tubing 28 and branching bore 27. Ball valve 130 is capable of moving through a range of horizontal positions (from the viewpoint of FIGS. 11–13), with the extremes of movement range being shown. In FIG. 12, ball 130 is restrained from further movement to the left by the presence of cross bar 132, which extends across an end of space 134, which space communicates with transverse bore 27. At the right limit of motion of ball 130, as shown in FIG. 13, ball 130 is stopped from movement by the smaller, inner diameter of branching tubing 28. However, as shown in both FIGS. 12 and 13, branch tubing 28 defines a cut-out portion 136. Thus, ball valve 130 has the rare characteristic of being intentionally disabled from completely sealing against flow between transverse bore 27 and tubing 28, although ball valve 130 in its position of FIG. 13 constricts and reduces the magnitude of that flow significantly.

Similarly, at the left hand position of FIG. 12, ball 130, resting against cross bar 134, still provides an open channel for flow of solution from solution source 40 through branch line 28 into transverse bore 27 and the main blood flow line comprising tubing sections 20 and 44.

The normal flow conditions within connector 24a are generally subatmospheric or negative pressure conditions, since connector 24a is upstream of pump 46. Ball 130 oscillates back and forth as the oscillatory negative pressure conditions created by pump 46 are transmitted through the liquid to the ball. As ball 130 oscillates into its right hand extreme position of FIG. 13, driven by pressure peaks of less negative pressure than the troughs of oscillatory pressure, it suppresses the transfer of liquid upstream into branch tubing 28, thus suppressing the fluid oscillations and pressure pulses that tend to disrupt blood-solution interface 106. Nevertheless, significant pressure changes in the system can pass through the barrier provided by ball 130 to reach pressure monitor 37, so that alarm conditions can be noted and signaled despite the flow restriction provided by ball 130, which tends to stabilize blood-solution interface 106.

If desired, the ball valve incorporating ball 130 could be placed in branch line 28 or in the bottom of chamber 29. Also, a duckbill-type valve imparting similar flow characteristics, or other valves, could be used.

Thus, the following effects are achieved:

1. Relatively free flow of saline from tube 30 to arterial line 12 when I.V. clamp 31 is opened. This is for the reason of quickly alleviating hypotensive episodes whenever they occur (as well as for rapid priming of the set to save the nurse time). Thus, the valve should be in an open position whether the driving pressure is only the head pressure of the saline bag 40 vs a near ambient pressure in the blood line (when blood pump 46 is off or flowing slowly) or when the driving pressure is high because the bloodline pressure is heavily negative due to the sucking of rapidly flowing bloodpump 46 against the restriction of the arterial fistula needle (not shown).

2. Suppression of blood pressure pulse when I.V. clamp 31 is closed and blood pump 46 is flowing. At low flows the pulse is neither strong or rapid and so the valve doesn't have to seat strongly (i.e. fluid can pass from the arterial line 12 to the I.V. line 28). Because the density of blood is greater than saline, the saline/blood interface 106 without intervention breaks down as the pulse quickens and hammers with increasing force. Thus, as the bloodpump 46 quickens its rotor speed (quicker pulses) and the blood pressure becomes more negative (higher flows sucking through the fistula needle) the force and the pace of the pressure pulse quickens. Further, at low flows and pressures the "volume" of the pulse is small so fluid passing back through the valve does not harm the blood/saline interface or move its position.

At high flows, the valve ball 130 seats somewhat more securely. It still passes fluid in order for the correct pressure to be read at transducer filter 36 (timed delayed because of the pulse suppression), but not so much as to give the blood pulse enough force and inertia to destroy the blood/saline interface. It should be noted that the pulse is typically from a higher negative to a lower negative pressure, rather than from a negative to a positive pressure.

Figure 15:
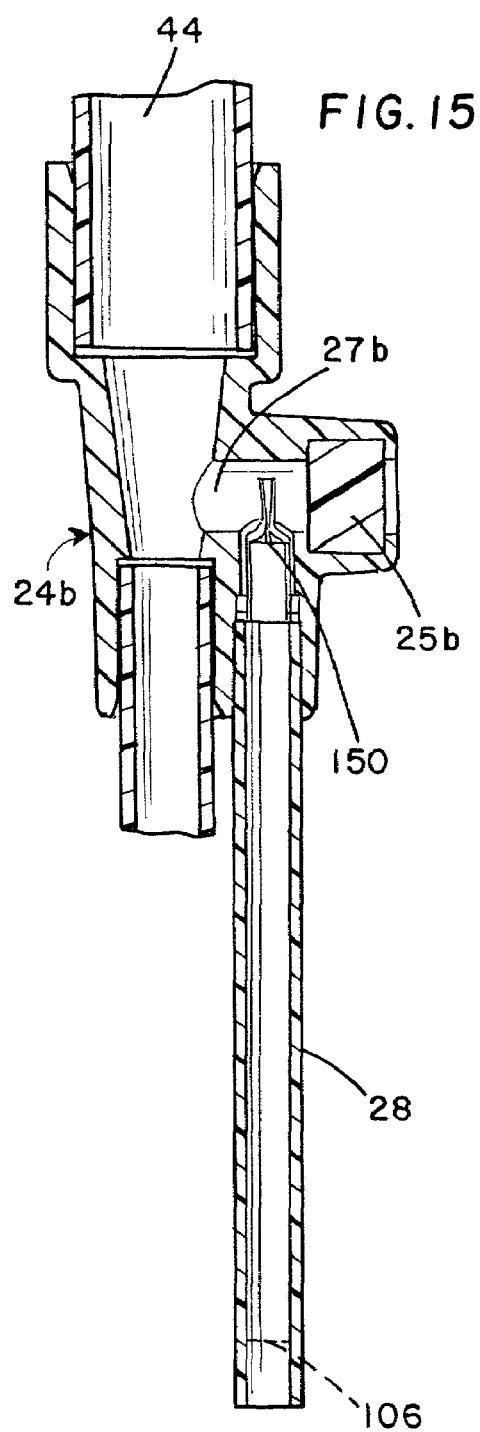
FIG. 15 is a longitudinal sectional view similar to FIG. 11, but showing an alternative embodiment in which the pulse suppression device is a partially disabled duckbill valve.
Figure 16:
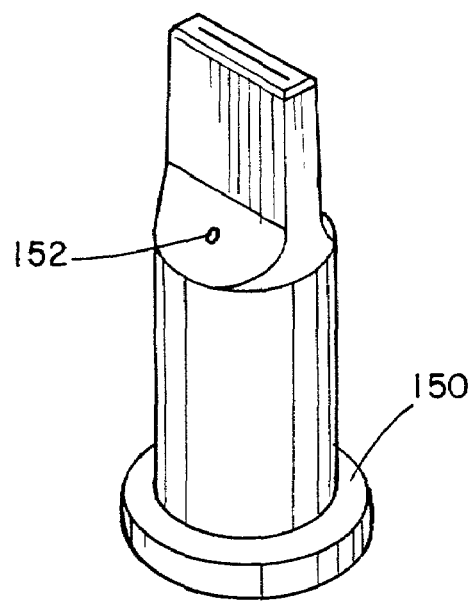
FIG. 16 is a front perspective view of the duckbill valve of FIG. 15.

The embodiment of FIGS. 15 and 16 how a common duckbill valve 150 can be modified and used to provide pulse suppression means of the type described above. FIG. 15 is similar in structure to FIG. 11, except for the type of pulse suppression means shown (the duckbill valve).

Branch line 28 from the set of FIG. 1 connects with connector 24b, which, like connector 24a, is positioned to provide double connection with pump tubing 44 and blood tubing 20. Injection site 25b is provided, being similar to injection site 25 of the previous embodiment. Transverse port 27b is similar to transverse port 27 of the previous embodiment, as are other components of connector 24b, except as otherwise described.

Particularly, the moveable ball 134 of the previous embodiment is replaced by duckbill valve 150, with valve 150 performing the same function as the moveable ball in the previous embodiment.

Referring to FIG. 16, a perspective view of duckbill valve 150 is shown. Valve 150 may be a common, commercially available rubber duckbill valve which operates as a one way valve in an entirely known manner. However, in accordance with this invention, one or more holes 152 are punched into valve 150, so that the permitted flow in the direction from connector 24b and through branch tubing 28 is restricted but not completely blocked, so that constant pressure communication between the blood line and branch tubing 28 is achieved moment-by-moment. At the same time, high volume flow through branch line 28 to connector 24b and from there to the blood flow circuit remains possible. Typically, the fluid backflow through duckbill valve 150 into branch line 28 can be about five percent of the forward liquid flow from branch line 28 into the blood flow circuit at pressures normally used, so that pressure pulses do not disrupt blood-solution interface 106.

FIGS. 17 and 18 show another embodiment of pulse suppression means in accordance with this invention.

FIG. 17 shows in line chamber 29a, serving as a substitute for chamber 29 in FIG. 1. The pulse suppression member 160 occupies chamber 29a, thus being positioned at the end 171 of branch line 28, which is opposed to the end of the branch line which connects with connectors 24, 24a, and 24b in the various embodiments. This shows the wide variability of the location of the pulse suppressing member for protection blood-solution interface 106. Chamber 29a connects at its bottom with branch tubing 28, and, like the embodiments of FIGS. 11–15, no sliding clamp like clamp 108 is required. At the top, chamber 29a may connect with tubing 30 which, in turn, connects with a pressure monitor 37. Chamber 29a also connects with tubing 38, which connects with the source of solution 40.

Chamber 29a carries a movable arrowhead member 160 as the pulse suppression means, which reciprocates for a short distance upwardly and downwardly in chamber 29a, being wider than and thus retained by constricted neck 162 of chamber 29a, through which constricted portion 163 of arrowhead member 160 extends. Head 164 of arrowhead member 160 is positioned above constricted neck 162 and, as shown in FIG. 18, is flattened on its respective sides as shown to provide a second dimension of width that is no more than half the wider dimension of width. Thus, when positive pressure is present in chamber 29a, there is still good room for flow of fluid out the bottom of chamber 29a, past the flat faces 166 of head 164 into tube 28. However, when a pressure pulse in branch line 28 is projected upwardly to arrowhead number 160, the pulse strikes flanged bottom 168 of arrowhead member 160, driving arrowhead member 160 upwardly so that flange 170 engages annular, constricted neck 162 of chamber 29a. However, this does not absolutely halt upward flow from tube 28 into chamber 29a, by the design of the system. Typically, one would engineer a valve-like structure of this type to seal well. However, in this instance, the system will be designed to seal only partially, providing a leaking upward flow that is at least one percent of the downward flow through the same system from chamber 29a. This can be accomplished in a variety of ways; by one or more longitudinal grooves or apertures in flange 170, by simply roughening the surface of flange 170 to allow a small amount of upward flow in all conditions, by adjustment of the draft angle in the vicinity of flange 170, or by a combination of these techniques.

Thus, as an oscillatory pressure from the blood line is provided through branch tube 28, arrowhead member 160 oscillates upwardly and downwardly, suppressing but not eliminating the flow and pressure communication between branch line 28 and chamber 29a. Thus, the pressure conditions are damped in branch line 28, having the effect of tending to preserve the integrity of blood-solution interface 106.

Inlet flow distribution member 172 has a closed bottom end, but allows the flow of solution to enter chamber 29a sideways through a plurality of apertures 176, so that the solution tends to impinge the wall of chamber 29a upon rapid infusion.

Another example of the pressure pulse suppression means may simply be provided by the use of a relatively enlarged diameter of branch tubing 28. For example, when a maximum flow through blood flow line 20, 44, 52 is about 500 ml. per minute and a two roller pump 46 is used pressure, pulses may be significantly suppressed by the use of a branch tube 28 having an inner diameter of at least 4.5 millimeters and preferably 5–8 mm. In a specific embodiment of this, pump segment tubing 44 may have an inner diameter of eight millimeters and an outer diameter of 12 millimeters. Thus, blood-solution interface 106 is not seriously disturbed by pressure oscillations, which oscillations are damped by the larger diameter tubing 28.

Further in accordance with this invention, venting line 88 may carry a connector 110 such as a female luer (FIGS. 1 and 7), which, by this invention, may be subsequently used for other purposes by retention of its aseptic condition while being used for venting. For example, it also can be connected to a solution or blood container in the event of an emergency.

A protector 112 is provided for connector 110, which protector comprises an outer sleeve 114, and a central, transverse wall 115 defined in outer sleeve 114. A male luer 116 projects axially within sleeve 114 from transverse wall 115 to engage the female luer connector 110 along with sleeve 114, so that the female luer connector 110 is enclosed within and without. A tube 118 projects axially within sleeve 112 from the transverse wall in the direction opposed to male luer 116, the tube and male luer having connected lumens 120. Tube 118 has an outer end that is substantially recessed within the sleeve 114. Thus, aseptic conditions can be retained as air and priming solution pass through tube 88 during priming and out of female luer 110, due to the protective action of the protector of this invention.

It should be noted that sleeve 114 may have an inner wall which is free of screw threads, but rather defines axially extending ribs 122 to facilitate axially sliding connection and retention with luer connector 110. Also, a hinged cap 124 may be attached to outer sleeve 114 in a position which permits closure of the cap over the outer sleeve end 126 that is opposed to the male luer 116, to surround and seal it.

By this means, the female luer connector 110, even though wet, can be aseptically protected so that it can be reused in another function during the blood treatment process if needed.

The above has been offered for illustrative purposes only, and is not intended to limit the scope of the invention of this application, which is as defined in the claims below.

What is claimed is:

1. A tubular medical set for the transfer of blood, said set having main blood flow tubing and a flexible branch tube connected in branching relation to the main tubing for connection to a source of physiological, cell-free solution and for retaining a blood-solution interface, said set further comprising a device to suppress pressure pulses tending to disrupt said blood-solution interface in said branch tube while allowing the transfer of pressure across said pressure pulse suppression means at essentially all times and permitting at any time the relatively unrestricted flow of said cell free solution through said branch tubing to the main blood flow tubing, said device to suppress pressure pulses comprising a moveable member that freely, by action of flowing fluid, moves through a range of positions, said device to suppress pressure pulses being designed to permit fluid flow in the direction opposed to said relatively unrestricted flow of said cell free solution in an amount 1 to 50 percent of the magnitude of said relatively unrestricted flow at maximum rate, under conditions of normal use.

2. The tubular medical set of claim 1 in which said moveable member comprises a ball.

3. The tubular medical set of claim 1 in which said device to suppress pressure pulses comprises a duckbill valve having an imperfection, causing the valve to permit large volume flow in one direction from the branch tube to the main blood flow tubing and a smaller volume of flow in the opposite direction.

4. The tubular medical set of claim 1 in which said pressure pulse suppression means comprises a moveable member having a central, reduced-width portion bracketed by enlarged-width portions for partial sealing, said moveable member being positioned in an in-line flow chamber in the flexible branch tube, said flow chamber defining an inwardly extending constriction which extends to retain said central, reduced-width portion of the moveable member, to permit said moveable member to reciprocate back and forth relative to said constriction so that one enlarged width portion or another enlarged width portion engages said constricted portion of the chamber so that bidirectional flow is permitted, the enlarged width portions being shaped whereby flow of liquid through said constricted portion in one direction is greater in magnitude than the liquid flow in the other direction under conditions of use, said one direction being from the branch tube to the main blood flow tubing.

5. The tubular medical set of claim 4 in which the increased-width portion pointing away from the main blood flow tubing defines a second dimension of width that is no more than about half a first dimension of width, to facilitate liquid flow.

6. A tubular medical fluid set comprising an in-line bubble trap chamber having a top wall and a tubular side wall, said top wall defining a port which communicates with flow tubing of said tubular set, said port communicating with a port tube extending longitudinally into said chamber adjacent to said side wall, said port tube having an inner tube end spaced below said top wall, said inner tube end directing flow out of said tube circumferentially of said bubble trap chamber, whereby medical fluid entering said chamber through said port is directed circumferentially about said chamber side wall, said chamber having a component which defines a baffle to convert circumferential flow above said tube end into turbulent flow, to prevent formation of a whirlpool having a significant, centrally depressed upper surface.

7. The tubular set of claim 6 in which said chamber defines a liquid level therein having a predetermined air volume which has a volume of at least 4 cc.

8. The tubular set of claim 6 in which said medical fluid in said chamber below said inner tube end is free to flow circumferentially without direct interference by a baffle.

9. The tubular set of claim 6 in which said baffle comprises a tube other than said port tube, said other tube being joined to an inner surface of a side wall of said bubble trap.

10. The tubular set of claim 6 in which said inner tube end defines a single flow inlet.

11. A tubular medical fluid set comprising an in-line bubble trap chamber having a top wall, a port communicating with flow tubing of the tubular set, said port communicating with a port tube extending into said chamber, said port tube having an inner tube end spaced below said top wall, said tube end being positioned to direct flow out of said tube circumferentially into the bubble trap chamber, whereby blood entering said chamber through said inner tube end is directed circumferentially about said chamber, said chamber having a component other than said port tube which serves as a baffle, said baffle being radially outwardly spaced from the center of said chamber and extending longitudinally along an upper portion of said chamber and terminating at a position above said port tube, to convert circumferential flow into turbulent flow at the level of said baffle, and to prevent formation of a blood whirlpool having a significant, centrally depressed upper surface, and whereby blood at about the level of the tube end and below is free to circumferentially flow without interference by the baffle.

12. The tubular set of claim 11 in which said baffle comprises a tube that is joined to an inner surface of a side wall of said bubble trap.

13. The tubular set of claim 12 in which said port tube also extends longitudinally and comprises a tube that is joined to an inner surface of a side wall of said bubble trap.

14. The tubular set of claim 11 in which said chamber defines a liquid level therein having a predetermined air volume which has a volume of at least 4 cc.

15. The tubular set of claim 11 in which said port tube also extends longitudinally and comprises a tube that is joined to an inner surface of a side wall of said bubble trap.

16. The tubular set of claim 11 in which said inner tube end defines a single flow inlet.

17. A tubular medical fluid set comprising an in-line bubble trap chamber having a top wall, a port communicating with flow tubing of the tubular set, said port communicating with a port tube extending longitudinally into said chamber within a side wall of said chamber while being spaced from the longitudinal axis of said bubble trap chamber, said port tube having an inner tube end spaced below said top wall, said inner tube end being positioned to direct flow out of said tube whereby blood entering said chamber through said inner tube end is directed circumferentially about said chamber, to provide circumferential flow of blood below said inner tube end, while blood in said chamber above said tube end is suppressed from substantial circumferential flow by the longitudinally extending port tube in said chamber, so that circumferential flow is converted into turbulent flow above said tube end.

18. The tubular set of claim 17 in which said medical fluid in said chamber below said inner tube end is free to flow circumferentially without direct interference by a baffle.

19. The tubular set of claim 17 in which said inner tube end defines a single flow inlet.

* * * * *